US010064667B2

(12) United States Patent
Leemrijse et al.

(10) Patent No.: US 10,064,667 B2
(45) Date of Patent: Sep. 4, 2018

(54) CALCANEUM TRANSLATION PLATE

(71) Applicant: BIOTECH ORTHO, Salon de Provence (FR)

(72) Inventors: Thibaut Leemrijse, Brussels (BE); Michel Maestro, Nice (FR); Bernhard Devos, Deurle (BE); Marc Relave, Andrezieu Boutheon (FR); Jean-Luc Besse, Chaponnay (FR)

(73) Assignee: TORNIER, Montbonnot-Saint-Martin (FR)

( * ) Notice: Subject to any disclaimer, the term of this patent is extended or adjusted under 35 U.S.C. 154(b) by 0 days.

(21) Appl. No.: 15/697,632

(22) Filed: Sep. 7, 2017

(65) Prior Publication Data

US 2017/0367743 A1 Dec. 28, 2017

Related U.S. Application Data

(63) Continuation of application No. 14/438,494, filed as application No. PCT/FR2013/052214 on Sep. 23, 2013, now Pat. No. 9,814,505.

(30) Foreign Application Priority Data

Oct. 29, 2012 (FR) .................................... 12 60297

(51) Int. Cl.
*A61B 17/80* (2006.01)

(52) U.S. Cl.
CPC ........ *A61B 17/8061* (2013.01); *A61B 17/809* (2013.01)

(58) Field of Classification Search
CPC .......................... A61B 17/8061; A61B 17/809
See application file for complete search history.

(56) References Cited

U.S. PATENT DOCUMENTS

| 4,446,857 | A | * | 5/1984 | Otte | ................... | A61B 17/7283 |
| | | | | | | 606/62 |
| 5,275,601 | A | * | 1/1994 | Gogolewski | ....... | A61B 17/8052 |
| | | | | | | 411/399 |
| 5,487,741 | A | * | 1/1996 | Maruyama | ........... | A61B 17/688 |
| | | | | | | 606/286 |
| 5,849,017 | A | * | 12/1998 | Reynolds | ............... | A61B 17/44 |
| | | | | | | 606/119 |

(Continued)

FOREIGN PATENT DOCUMENTS

WO 2010030960 A1 3/2010

OTHER PUBLICATIONS

International Search Report for corresponding International Application No. PCT/FR2013/052214.

*Primary Examiner* — Christian Sevilla
(74) *Attorney, Agent, or Firm* — Duane Morris LLP

(57) ABSTRACT

A calcaneum translation plate (1) characterized in that it comprises two end portions, i.e. a proximal anchoring portion (2) and a distal fixing portion (3), oriented in opposing directions and arranged in spaced parallel planes (P-P, P'-P'), said proximal and distal portions connecting to an intermediate portion (4) having a square general profile and comprising two perpendicular bearing surfaces, the proximal anchoring portion extending from one (5) of said surfaces and perpendicular thereto, whereas the distal fixing portion extends in the extension of the other bearing surface (6).

11 Claims, 3 Drawing Sheets

(56) References Cited

U.S. PATENT DOCUMENTS

| | | | | |
|---|---|---|---|---|
| 8,764,807 B2* | 7/2014 | Michel | A61B 17/15 606/280 |
| 9,295,506 B2* | 3/2016 | Raven, III | A61B 17/80 |
| 9,814,474 B2* | 11/2017 | Montoya | A61B 17/1728 |
| 9,814,505 B2* | 11/2017 | Leemrijse | A61B 17/809 |
| 2005/0228390 A1* | 10/2005 | Cutshall | A61B 17/1666 606/81 |
| 2006/0074444 A1* | 4/2006 | Lin | A61B 17/00008 606/190 |
| 2008/0108997 A1* | 5/2008 | Berrevoets | A61B 17/7044 606/251 |
| 2008/0167658 A1* | 7/2008 | Kerr | A61B 17/68 606/93 |
| 2009/0281582 A1* | 11/2009 | Villa | A61B 17/7086 606/86 A |
| 2011/0009866 A1* | 1/2011 | Johnson | A61B 17/8014 606/70 |
| 2011/0230969 A1* | 9/2011 | Biedermann | A61B 17/8047 623/17.16 |
| 2011/0276097 A1* | 11/2011 | Raven, III | A61B 17/8061 606/284 |
| 2011/0306977 A1* | 12/2011 | Michel | A61B 17/15 606/71 |
| 2012/0209334 A1* | 8/2012 | Lewis | A61B 17/8014 606/286 |
| 2014/0066995 A1* | 3/2014 | McCormick | A61B 17/1728 606/281 |
| 2015/0257803 A1* | 9/2015 | Sampath | A61B 17/8023 606/71 |
| 2015/0272642 A1* | 10/2015 | Leemrijse | A61B 17/809 606/291 |
| 2016/0228257 A1* | 8/2016 | Predick | A61F 2/4202 |
| 2017/0042599 A1* | 2/2017 | Bays | A61B 17/8866 |
| 2017/0325859 A1* | 11/2017 | DaCosta | A61B 17/8057 |
| 2017/0360488 A1* | 12/2017 | Kowalczyk | A61B 17/8095 |

* cited by examiner

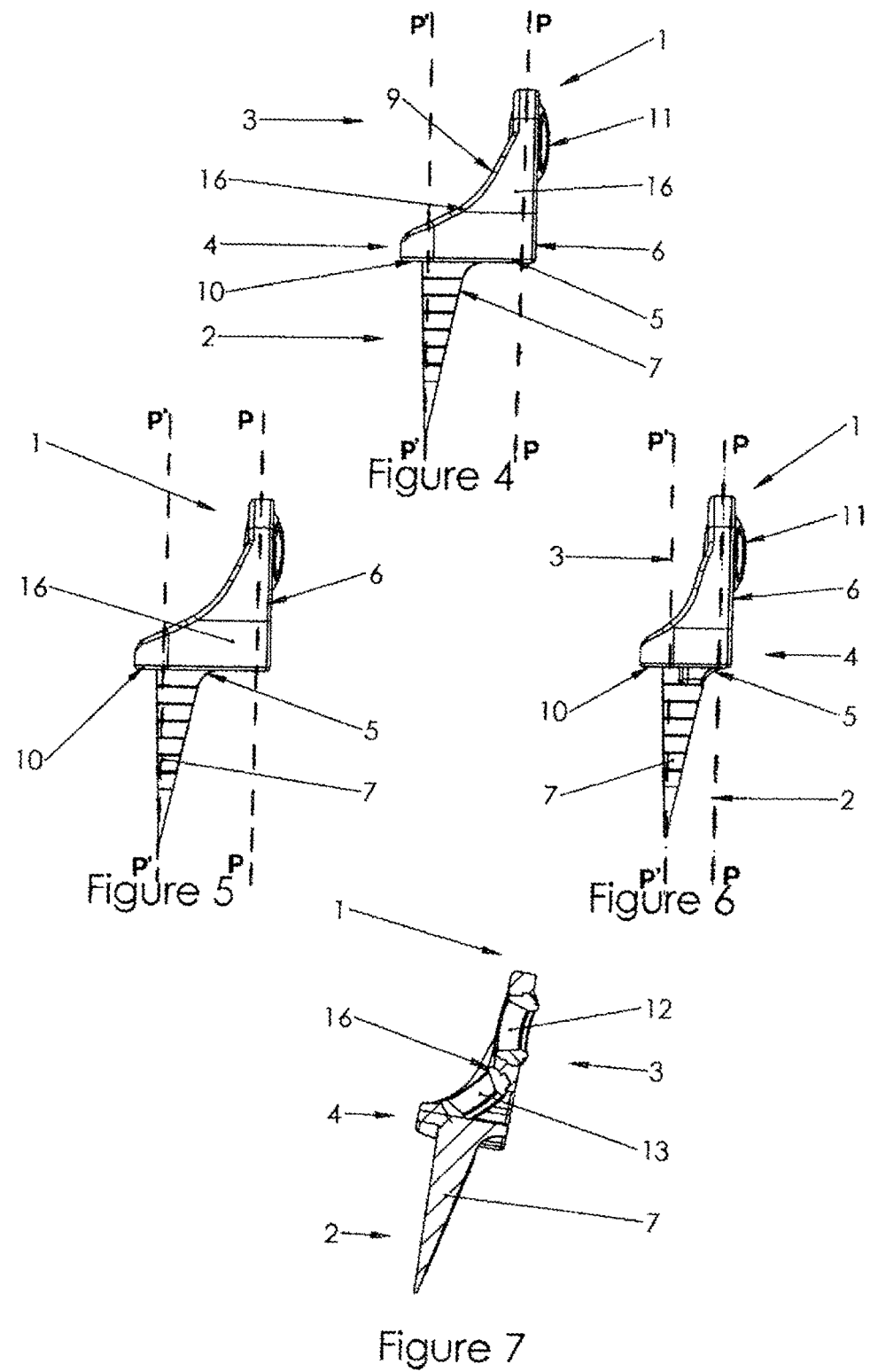

CALCANEUM TRANSLATION PLATE

CROSS-REFERENCE TO RELATED APPLICATIONS

This application is a Continuation of U.S. patent application Ser. No. 14/438,494, filed Apr. 24, 2015, which is a U.S. national stage application under 35 U.S.C. § 371 of International Application No. PCT/FR2013/052214, filed Sep. 23, 2013, which claims priority to French patent application No. 12/60297, filed Oct. 29, 2012, the entireties of which are incorporated herein by reference.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to the field of corrective orthopedic surgery.

It concerns an implant intended for osteotomy operations. More precisely, the invention is relative to a calcanean translation plate.

2. Description of Related Art Including Information Disclosed Under 37 CFR 1.97 and 37 CFR 1.98

The skeletal bones of human beings and vertebrates generally consist of at least two areas: a rigid cortical area and an internal spongy area of more tender consistency which may itself, for certain bones, be traversed by a marrowy canal enclosing soft tissues.

The human hindfoot is essentially comprised of two bones: the ankle-bone (or astragalus) above which is placed on the calcaneum below. The calcaneum is a short bone, even and asymmetric, of elongated shape from the rear end forward and flattened across. The association of the calcaneum and the ankle-bone forms the heel on which rests most of the body's weight. This part of the foot is therefore subject to heavy pressures which makes it prone to various malformations, sources of pain and difficulty and/or incapability of walking for the patients.

It is sometimes indispensable to correct the shape of the calcaneum. The intervention consists of an osteotomy of said bone with medialization of the large tuberosity, i.e. the section of the calcaneum into two parts and the displacement of one in relation to the other. This will allow a better support of the hindfoot and above all reducing the internal constraints on the muscles and ligaments.

Osteotomy designates the surgical section of a long bone in order to modify its axis, size or shape for therapeutic or plastic purposes; it is directed at restituting better axes to long bones in order to better distribute the pressures on the corresponding articulations. Then, the principle is either to cut out a slice over the width of the bone, and to refasten the remaining pieces after having removed it, or to simply cut across and to open the space of one side, by filling the void created with a bone graft, depending on whether one wants to close an angle or open it. Osteotomy may also be followed by a translation, i.e. the shifting of one of the parts of the bone resulting from this section.

This operation requires the installation of support systems for the calcaneum in order to keep the translation in place. As far as the calcaneum is concerned, this part of the foot being subjected to very strong pressures due to the weight of the body and its role in walking, the major difficulty is to produce orthopedic systems that are sufficiently stable and rigid to remain in place and maintain the translation of the calcaneum.

One knows of calcanean implants of diverse and varied shapes, but the perpetuation of the system, i.e. its lasting stability and rigidity, is often uncertain because the implant rests generally in the spongy part of the calcaneum, in spite of the locally harder thalamic crossings, which leads to a rotation of the system as well as a slipping of the latter under the effect of the forces of the body's weight and the porosity of the spongy part of the bone.

For example, the document US-2011/009.866 describes a system for osteotomy composed of a plate which includes two ends aligned along a longitudinal axis fitting together through a median portion and screws. The first end includes a cutting edge and a hole which receives a non-interlocking screw and presents a chamfer which narrows from a lesser thickness at the edge in the direction of the hole, the second end has a locking hole which receives a safety screw, and the first and the second hole are aligned along the longitudinal axis.

The drawback of this device is primarily the lack of stability: as a matter of fact, the configuration of this implant does not allow it to be supported by the cortical of the proximal end of the calcaneum. Its only support therefore is the spongy bone which is porous. In view of the extremely strong forces being applied to this bone, in particular during walks, this system is liable to enter into rotation or slide in the spongy part of the proximal portion of the calcaneum which makes it very unstable and presents major risks for the patient.

Also known are calcanean implants which have no compressive effects on the orthopedic screws allowing their fixing, or for which the locking of said screws is done with a metal-metal coupling which leads, over time, to a cold solder of the galvanic couple leading to toxic corrosion for the patient and making the later removal of the screws impossible.

Furthermore, these implants present the drawback of requiring particularly invasive surgery for their installation, forcing the practitioner to make significant opening incisions over the entire lateral portion of the calcaneum.

BRIEF SUMMARY OF THE INVENTION

One aim of the present invention is to remedy the drawbacks cited above by providing an implant capable of perennating, i.e. stabilizing and stiffening, the system created by the translation of the calcaneum.

According to the invention, this aim has been achieved by a calcaneum translation plate or implant, comprised of two end portions, i.e. a proximal anchoring portion and a distal fixing portion oriented in opposing directions and arranged in spaced parallel planes, said proximal and distal portions connecting to the third intermediate portion presenting a general square profile and featuring two perpendicular bearing surfaces, the proximal anchoring portion extending from one of these surfaces and perpendicular thereto, whereas the distal fixing portion extends in the prolongation of the other bearing surface.

According to another characteristic arrangement, the proximal anchoring portion is constituted by a blade with a narrowing profile in the direction of its free end.

An advantageous implementation consists of providing said blade with anti-backoff teeth preventing the rotation of the implant after its installation. Preferably these anti-backoff teeth are present on the lateral edges of the proximal anchoring portion.

According to a preferred implementation, the intermediate portion presents a shoulder at its bearing surface at the proximal portion of the implant. After the installation of the plate, said shoulder abuts against the thin cortical of the proximal end of the calcaneum and thus prevents the plate from sliding into the spongy part of the bone.

According to a characteristic implementation of the invention, the distal portion of the plate features at least one hole for the passage of at least one fastening screw.

The intermediate portion of the plate may present a concavity which can accommodate one or several holes for the passage of one or several fastening screws. Advantageously, the distal and intermediate portions each have two screw holes, the axis of the holes in the intermediate portion being inclined relative to the axis of the screw holes of the distal face. Preferably, said holes have a conical shape.

According to a preferred implementation, the distal portion of the plate presents some embossing on its face in contact with the bone.

Remarkably, the intermediate portion of said plate presents reinforcement gussets on its lateral edges.

BRIEF DESCRIPTION OF THE DRAWINGS

The aims, characteristics and advantages mentioned above and still more, will become clearer in the detailed description below and the attached drawings in which:

FIG. 4 is a side view of the calcanean translation plate according to the invention.

FIGS. 5 and 6 illustrate, as examples, different implementations of the plate according to the invention, constituting a part of a set of implants that may be presented to the practitioner.

FIG. 7 is a longitudinal section, at a larger scale, along the line 7-7 of FIG. 1.

Figure 1:
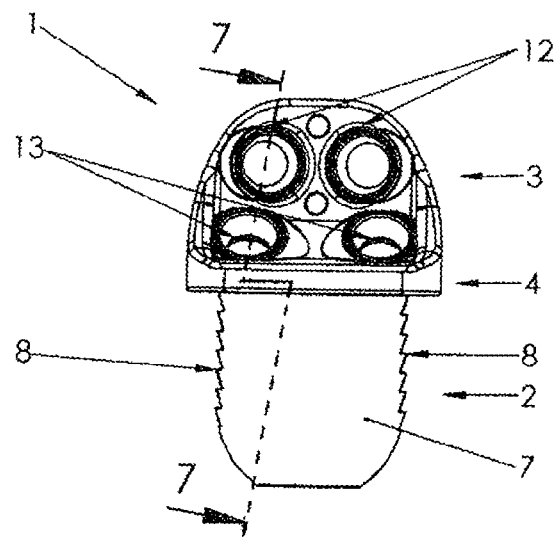
FIG. 1 is a front view of the calcanean translation plate according to the invention.

Reference to said drawings is made to describe an interesting, although by no means limiting, example of implementation of the calcaneum translation plate according to the invention.

DETAILED DESCRIPTION OF THE INVENTION

The term "distal" designates the portion or end of a bone which is the farthest away from the root of this bone. The term "proximal" designates the portion or end of a bone which is the closest to its fixing point. Here, the proximal end of the calcaneum is the one that is attached to the ankle-bone and to the rest of the bones of the foot, the distal portion or end of the calcaneum designating the end of the bone which osteotomy separates from the rest of the body. Likewise, the proximal and distal portions of the implant are defined depending on whether their bearing surface is the proximal or distal end of the calcaneum.

According to the invention, the objective has been achieved by an implant consisting of a plate 1 which is comprised of three parts: a proximal anchoring portion 2, a distal fixing portion 3 and an intermediate portion 4 which connects them. The distal and proximal portions 2 and 3 are oriented in opposing directions and positioned in spaced parallel planes P-P, P'-P', and present a generally rectangular shape. The ergonomic design of the plates reduces friction with the skin as well as detection of the implant once it is installed.

The first proximal anchoring portion 2 is meant to insert itself in the spongy bone of the proximal end of the calcaneum, the second portion is a fixing face 3 and meant to place itself on the cortical surface of the distal end of the calcaneum as its bearing surface, thus stabilizing the portion of the bone that has been separated from the rest of the skeleton by the osteotomy. Said distal and proximal portions 3 and 2 are attached to an intermediate portion 4 presenting a generally square profile and featuring two perpendicular bearing surfaces 5 and 6, the proximal anchoring portion extending from one of these surfaces 5 and perpendicularly to it, whereas the distal fixing portion extends in the prolongation of the other bearing surface 6.

The proximal and distal portions 2 and 3 are thus not aligned but set off by said intermediate zone 4 which separates them.

Advantageously, the proximal anchoring portion of the plate according to the invention may be constituted by a blade 7 presenting a narrowing profile in the direction of its free end so as to form a cutting edge.

According to a characteristic arrangement of the invention the proximal anchoring portion 2 of the implant, i.e. the one meant to be inserted in the spongy layer of the proximal end of the calcaneum, presents anti-backoff teeth 8 which prevent the implant from dislodging itself and stop it from rotating once it is inserted in the bone. These anti-backoff teeth are, for example, placed on the lateral edges of said proximal portion 2.

According to a characteristic arrangement of the invention, the intermediate portion 4 of the plate has a concavity 9 on its bearing surface 6 from which extends the distal fixing portion 3 of the place and a shoulder 10 at its bearing surface 5 meant for the proximal anchoring portion 2 of the plate. In the position of use, the anchoring portion 2 being inserted in the spongy layer of the bone, said shoulder 10 bears against the cortical layer of the proximal portion of the calcaneum in order to stabilize the system and to prevent it from slipping into this spongy part of the bone under the effect of the forces generated by the weight of the body.

According to a preferred implementation, the distal fixing portion 3 of the plate 1 presents an embossed area 11 to prevent the crushing and damaging of the periosteum. The periosteum is the vascularized membrane which covers the entire surface of the bones (with the exception of the articular cartilage) and contains the blood vessels which carry the nutrients that are indispensable for their repair. Any damage to the periosteum leads to the bone becoming incapable of regenerating itself, and even to its necrosis. This embossing 11 allows safeguarding the periosteum by offering punctual bearing surfaces to the plate 1, and not a surface-wide load which compresses the periosteum and damages it, as is usually the case with calcanean implants.

According to one implementation of the invention, the distal fixing portion 3 of the plate features at least one hole 12 for the passage of at least one fastening screw.

According to one example of implementation, the intermediate portion presents a concavity 9 which may typically feature one or several holes 13 for the passage of one or several fastening screws (15). Preferably, the distal portion 3 of the implant as well as the intermediate portion 4 are both provided with holes 12 and 13 for the passage of the screws, the axis of the holes 13 of the intermediate portion being inclined relative to the axis of the holes 12 of the distal portion.

On the other hand, the translation plate of the calcaneum 1 according to the invention does not have any holes in the end of the proximal anchoring portion 2.

Figure 2:
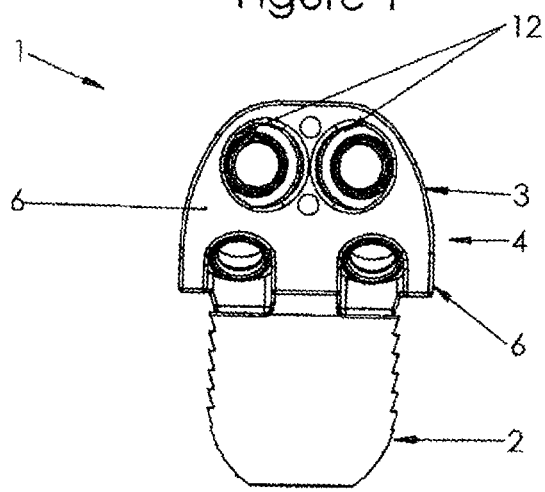
FIG. 2 is a rear view of FIG. 1.
Figure 3:
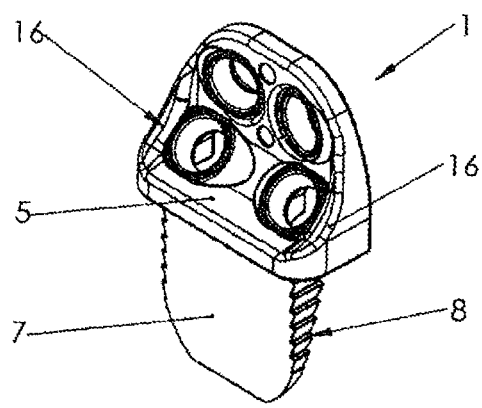
FIG. 3 is a perspective view of the plate according to the invention.
Figure 8:
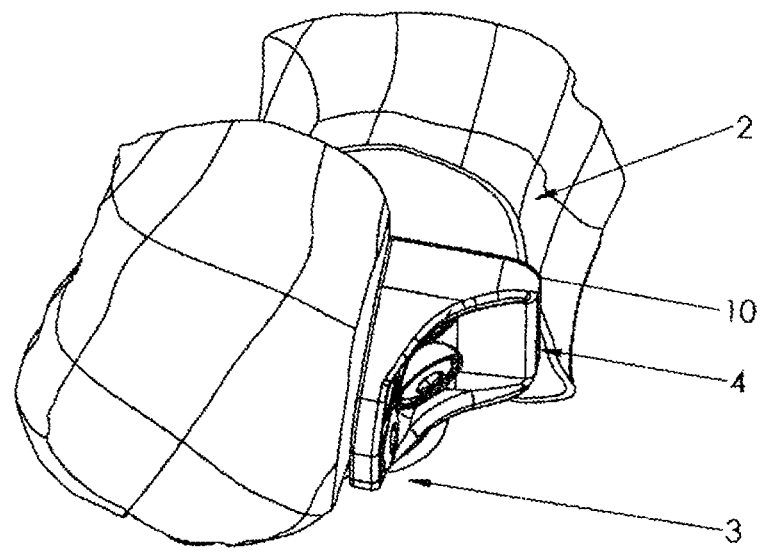
FIG. 8 is a perspective view of the hindfoot showing the calcaneum translation plate according to the invention in the position of use, the distal and proximal portions of the calcaneum being shown in transparency.
Figure 9:
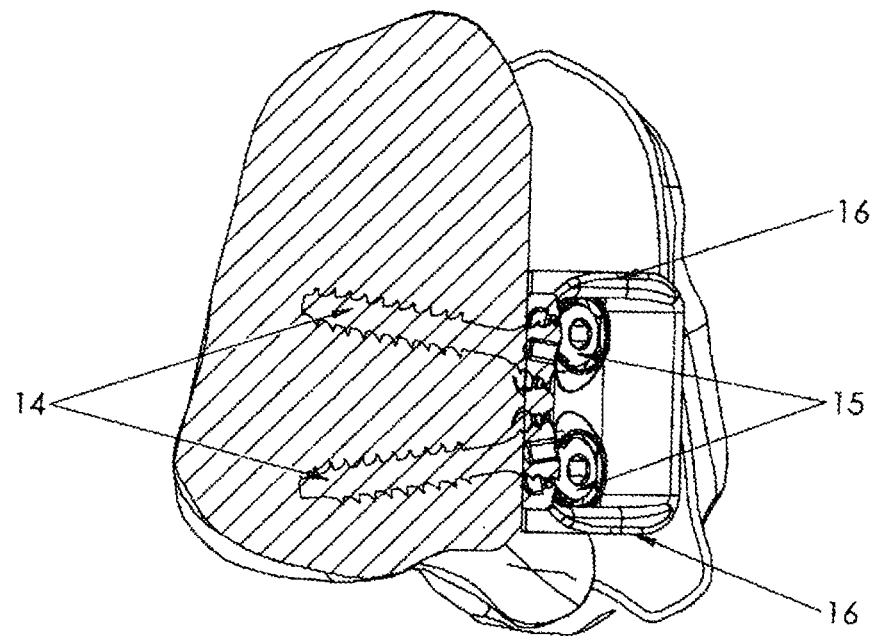
FIG. 9 is a detailed front view and at a larger scale, showing the bearing surface of the shoulder of the intermediate portion of the plate against the cortical of the proximal portion of the calcaneum.

According to the example illustrated in FIGS. 1 to 3, the distal 3 and intermediate 4 portions each present two holes for the passage of the screws, said holes may present a conical shape. The large opening of the holes accessible from the inside of the plate constitutes the entrance of these, whereas the small opening of said holes opens on the outside of the plate meant to be applied against the cortical of the distal end of the calcaneum as far as the distal face of the plate is concerned, and against the spongy portion of the proximal end of the calcaneum for the concavity of the intermediate portion.

The calcanean translation plate 1 according to the invention consists of a biocompatible, rigid but expansible material, to allow locking of the screw heads while ensuring sufficient rigidity to fasten together the two portions of the bone created by the osteotomy.

For example, plate 1 is made of polyetheretherketone (PEEK), for example of the type commercialized under the registered brand name "PEEK-OPTIA".

According to an advantageous implementation, the lateral walls of the hole passages 12 and 13 meant to receive the heads of orthopedic screws 14 and 15 are expansible in the radial direction so as to permit the compression of said screw heads which are inserted there, thereby ensuring the locking or blocking of the screws in the calcanean translation plate and preventing any possibility of backward movement after having been screwed into the bone material, which makes the translation resulting from the osteotomy operation permanent.

The screws 15 locking themselves in the holes 13 of the intermediate portion 4 do already have an angle of divergence which increases the holding force of the device and the maintenance in several planes. The locking action enables the screws 14 and 15 to become integral with the plate.

According to one implementation, the screws 15 which are seated in the proximal end of the calcaneum are already angled between 10° and 50°. According to an advantageous implementation, at least one of the screws used with the plate according to the invention has a threaded head.

Advantageously, the biocompatible material constituting the implant contains 30% carbon fibers which permits its future retrieval if need be, while ensuring the necessary rigidity.

According to one implementation, the locking of the screw heads in PEEK (compression) is inspired by the patented system (FR-2.845.588 "Selfblocking Device of osteosynthesis" in the name of Biotech International) and designated by the registered brand name "EASYLOCK".

According to a characteristic example, the intermediate portion 4 of plate 1 according to the invention presents reinforcing gussets 16 on its lateral edges.

According to an advantageous implementation of the invention, the portions of the plate that are not in contact with the bone, i.e. the intermediate portion 4 which has a square-shaped profile, the face of the distal portion of the plate which is not bearing against the bone as well as the possibly present gussets 16, present rounded edges so as to increase the contact surface and to reduce the angle of contact in order to avoid any lesions caused by the friction coefficient between the skin and the translation plate.

In order to enable adaptation to the specific needs of the patient, each case being different, the implants according to the invention will be made available to surgeons in the form of sets each consisting of a plurality of calcanean translation plates of different dimensions (for example FIGS. 4, 5, and 6).

The calcanean translation plate according to the invention offers several interesting advantages and in particular:
Very great stability;
No space requirement for screw heads outside of the plate;
Anatomical conformance of the plate which adapts to the shape of the bone;
Very good resistance to the weight of walking.

The invention claimed is:

1. Calcaneum translation plate, wherein the calcaneum translation plate comprises two end portions, i.e. a proximal anchoring portion and a distal fixing portion which are oriented in opposing directions and which are arranged respectively in a proximal plane and in a distal plane, the proximal and distal planes being spaced and parallel, wherein said proximal and distal portions are connected to an intermediate portion presenting a square general profile and featuring two perpendicular bearing surfaces, wherein the proximal anchoring portion extends from one of these bearing surfaces and perpendicularly thereto, whereas the distal fixing portion extends in the prolongation of the other bearing surface, and wherein the intermediate portion presents a shoulder at the bearing surface from which the proximal anchoring portion extends, the shoulder being located on a side of the proximal plane, opposed to the distal plane.

2. Calcaneum translation plate according to claim 1, wherein the distal fixing portion features at least one hole for passage of at least one fastening screw.

3. Calcaneum translation plate according to claim 1, wherein the intermediate portion presents a concavity featuring one or several holes for passage of one or several fastening screws.

4. Calcaneum translation plate according to claim 1, wherein the distal and intermediate portions are both provided with holes for passage of screws, an axis of a hole of the intermediate portion being inclined relative to an axis of a hole of the distal fixing portion.

5. Calcaneum translation plate according to claim 4, wherein the distal and intermediate portions each present two holes for passage of screws.

6. Calcaneum translation plate according to claim 2, wherein said at least one hole has a conical shape.

7. Calcaneum translation plate according to claim 1, wherein the distal fixing portion presents an embossing on a face intended to come into contact with the bone.

8. Calcaneum translation plate according to claim 1, wherein the intermediate portion presents, on its lateral edges, reinforcing gussets.

9. Calcaneum translation plate according to claim 3, wherein said one or several holes have a conical shape.

10. Calcaneum translation plate according to claim 1, wherein the proximal anchoring portion does not have any holes.

11. Calcaneum translation plate according to claim 1, wherein the proximal anchoring portion is designed to be inserted into calcaneum spongy bone.

* * * * *